(12) United States Patent
Gill

(10) Patent No.: US 9,504,802 B2
(45) Date of Patent: Nov. 29, 2016

(54) GUIDING CATHETER STABILIZATION SYSTEM

(75) Inventor: Sukhjit Gill, Oakbrook, IL (US)

(73) Assignee: Sukhjit Gill, Oakbrook, IL (US)

( * ) Notice: Subject to any disclaimer, the term of this patent is extended or adjusted under 35 U.S.C. 154(b) by 1133 days.

(21) Appl. No.: 13/179,396

(22) Filed: Jul. 8, 2011

(65) Prior Publication Data

US 2012/0016343 A1    Jan. 19, 2012

Related U.S. Application Data

(60) Provisional application No. 61/365,770, filed on Jul. 19, 2010.

(51) Int. Cl.
*A61M 25/00* (2006.01)
*A61M 25/06* (2006.01)

(52) U.S. Cl.
CPC ..... *A61M 25/0043* (2013.01); *A61M 25/0662* (2013.01); *A61M 25/0026* (2013.01); *A61M 2025/0063* (2013.01)

(58) Field of Classification Search
CPC ............... A61M 2025/0063; A61M 25/0662; A61M 2025/0062; A61M 25/0043; A61M 25/0068; A61M 25/003; A61M 2025/0037; A61M 25/0041; A61M 25/0169; A61M 25/09; A61M 5/158; A61M 2025/0183; A61M 2025/09125; A61M 2210/125; A61M 2210/127; A61M 25/005; A61M 25/0053; A61M 25/01; A61M 25/09041; A61M 1/3666; A61M 2025/0079; A61M 2025/018; A61M 2025/0681; A61M 2039/0232; A61M 25/0012; A61M 25/0144; A61M 25/0026; A61M 2025/1052; A61M 25/1011; A61M 2025/0002; A61M 2025/0004; A61M 2025/0034; A61M 2025/0073; A61M 2025/0081; A61M 2025/1063; A61M 25/0032; A61M 25/0069; A61M 25/0074; A61M 25/008; A61M 25/0082; A61M 25/1029; A61M 25/104; A61M 2025/0018; A61M 2025/1056; A61M 2025/1079; A61M 25/0045; A61M 25/0127; A61M 25/10; A61M 25/1027; A61M 25/1034

USPC ............................................. 604/528, 164.01
See application file for complete search history.

(56) References Cited

U.S. PATENT DOCUMENTS

| | | | | |
|---|---|---|---|---|
| 5,230,348 | A * | 7/1993 | Ishibe et al. | 600/585 |
| 5,439,445 | A * | 8/1995 | Kontos | A61F 2/88 604/103.1 |
| 6,733,486 | B1 * | 5/2004 | Lee et al. | 604/525 |
| 7,369,901 | B1 * | 5/2008 | Morgan | A61N 1/059 600/375 |
| 2005/0070998 | A1* | 3/2005 | Rourke et al. | 623/2.11 |
| 2005/0131343 | A1* | 6/2005 | Abrams | A61M 25/0662 604/95.04 |
| 2006/0064056 | A1* | 3/2006 | Coyle | A61M 25/0041 604/96.01 |

(Continued)

*Primary Examiner* — Bhisma Mehta
*Assistant Examiner* — Brandy S Lee
(74) *Attorney, Agent, or Firm* — Convergence Intellectual Property Law P.C.; Jonathan Garfinkel

(57) ABSTRACT

Guiding catheter support devices, systems, and methods for stabilizing a guiding catheter while positioned in a vessel of a patient are disclosed. The device comprises a stabilizing wire with an elongate portion and a fortified end, wherein the fortified end is more rigid than the elongate portion. The stabilizing wire is inserted into a guiding catheter while it is positioned in a vessel of a patient and increases the rigidity of at least a portion of the guiding catheter thereby providing support and stabilizing the catheter. A standard guiding catheter may be used or a guiding catheter with a primary lumen and a stabilization lumen having a blind distal end may be used, wherein the stabilizing wire is inserted into the stabilization lumen.

10 Claims, 7 Drawing Sheets

(56) References Cited

U.S. PATENT DOCUMENTS

| | | | |
|---|---|---|---|
| 2006/0064058 A1* | 3/2006 | Coyle | A61M 25/0082 604/103.04 |
| 2006/0264907 A1* | 11/2006 | Eskridge et al. | 604/528 |
| 2007/0250039 A1* | 10/2007 | Lobbins | A61M 25/0012 604/523 |
| 2007/0288090 A1* | 12/2007 | Solem et al. | 623/2.37 |
| 2008/0082051 A1* | 4/2008 | Miller et al. | 604/164.13 |

* cited by examiner

GUIDING CATHETER STABILIZATION SYSTEM

CROSS-REFERENCES TO RELATED APPLICATIONS

This application claims the benefit and priority of U.S. Provisional Application No. 61/365,770, filed on Jul. 19, 2010, the full disclosure of which is incorporated herein by reference.

FIELD OF THE INVENTION

The present invention relates generally to devices, systems and methods for stabilizing a guiding catheter inside a vessel of a patient.

DESCRIPTION OF THE RELATED ART

Coronary artery disease is the most common cause of death in the adult population in both sexes in the United States of America. This consists of the development of a blockage in the coronary artery and usually has serious consequences, such as a heart attack, if not treated in a proper, safe and timely fashion, especially once these lesions become seventy to eighty percent obstructive. The cause of blockage could be the deposition of atheromatous plaque, old thrombus or similar other deposits in the body vessel. When these coronary lesions become very severe, they can either be treated by percutaneous coronary intervention (PCI) using catheters or coronary bypass surgery. A popular method of removal of such occlusions is by PCI as it is less invasive than surgery.

PCI may include the following steps: A) Coronary cannulation: A guiding catheter is advanced through the femoral artery near the groin area to the ostium of the coronary arteries carrying the lesions. Radiopaque contrast may be then injected to identify the site of blockage in the lumens of the vasculature. B) Guidewire placement: A soft nontraumatic guidewire is advanced through the guiding catheter. This guidewire crosses the obstructive lesion and is advanced through the entire length of the vessel. This guidewire acts as a track over which further instrumentation is advanced. C) Stent deployment: After the wire is properly positioned, a catheter that carries a stent at its distal end over an inflatable part of this catheter is advanced inside the guiding catheter and over the guidewire. The stent is positioned accurately at the site of the blockage. After the stent has been properly positioned the balloon is inflated thus releasing the stent and at the same time flattening the plaque.

The guiding catheter must be flexible and of preformed shape such as Judkins, Amplatz, or hockey stick. These catheters have varying degrees of ease of insertion and provide varying degrees of support. There is a tradeoff between ease of insertion and support. Catheters that provide less support are easier to successfully navigate to the target vessel and catheters that provide greater support are harder to navigate. The lack of sufficient support becomes a problem when force is applied to advance the guidewire through the guiding catheter and often leads to the catheter disengaging from the ostium of the coronary artery. Once the guiding catheter disengages, there can be no further advancement of the guidewire or the stent over the guidewire.

The coronary arteries that require PCI range from 2 mm to 5 mm in diameter. More than ninety percent of these arteries range from 2.5 mm to 3.5 mm. In order to qualify for PCI, the obstructive lesion must block from seventy to eighty percent of the diameter of the vessel. This leaves less than 1 mm of the lumen available to perform the procedure. The diameter of an uninflated balloon, with or without a stent is over 1 mm. Although the shaft of all PCI balloons is strong enough to push the balloon through the lesion, its pushability depends on the ability of the guiding catheter to stay engaged in the ostium of the coronary artery. Often, as one tries to push the stent through the lesion the guiding catheter dislodges from the ostium of the coronary artery. This makes it impossible to get the stent through the lesion and results in the removal of the equipment in order to try a different guiding catheter, guidewire, stent catheter or any combination of these. In many cases this leads to abandoning the procedure. Therefore, sufficient guiding catheter support is mandatory in order to complete the procedure and carry the PCI equipment through the lesion.

Some guiding catheters are very flexible and are easy to engage in the coronary artery. However, these guiding catheters have very little support and have a high chance of disengaging. Other guiding catheters provide more support but are less flexible and are much more difficult to engage requiring more experience and maneuvering. This leads to increased procedure time and radiation exposure. A need exists for a catheter that is both easy to cannulate and provides sufficient support.

U.S. Pat. No. 5,098,412 to Shiu et al. describes a guiding catheter with a primary lumen and a secondary lumen where the primary lumen and the secondary lumen are present at the proximal portion of the catheter but are not present at the distal portion. A linearly incompressible flexible elongate element is slidable within the secondary lumen. The elongate element exits the secondary lumen at its distal end and connects to the outside of the primary lumen at its distal end. Using a slider on the outside of the secondary lumen the operator moves the elongate element further into the catheter causing the secondary lumen to push away from the primary lumen at its distal end and brace against the vessel wall providing support. However, this requires the use of a special guiding catheter. If an operator attempts a procedure using a traditional guiding catheter and determines that the traditional guiding catheter does not provide sufficient support, the operator would have to remove the equipment in order to use this special guiding catheter with more support. Inadvertent separation of the distal portions of the catheter may make cannulation more difficult. Also, if the elongate element is flexible enough to easily cannulate then it may not provide sufficient support when braced against the wall of the vessel.

U.S. Patent Application No. 2008/172036 to Stys et al. discloses a guiding catheter comprising a first catheter and a second catheter designed to be moved together within a vessel. The second catheter is within the first catheter. The two catheters have different stiffness and different curves at their distal ends. Relative movement of the two catheters by the operator changes the shape and stiffness of the distal end of the guiding catheter. Again this requires the use of a special guiding catheter and the removal of equipment if a traditional catheter is used. The use of two catheters as a guiding catheter demands increased skill to properly use the catheter. It may also cause size issues because it must be large enough to fit a third catheter within it to deploy the stent.

U.S. Pat. No. 4,822,345 to Danforth et al. discloses a guiding catheter with a balloon which extends along the exterior surface of the catheter. The balloon is inflatable and deflatable by the operator while the catheter is within a vessel. When inflated the balloon adds to the rigidity of the catheter. However this too requires the use of a special guiding catheter and may require more skill to use. The Danforth patent also discloses the use of stiff wires to increase the rigidity of the guiding catheter once it is positioned. In this embodiment, the stiff wires are bent to the correct shape and then inserted into the catheter. This device is not preferred because of the difficulty involved in bending stiff wires to the correct shape before inserting them and inserting stiff bent wires into a curved and positioned catheter. It also lacks a way of keeping the wires in place once positioned. The Danforth patent further discloses the use of flexible wires built into the guiding catheter. The flexible wires are connected to the distal end of the catheter. After the catheter is positioned, tension is applied to the wires to increase stiffness. Again this requires the use of a special guiding catheter and may require more skill to use.

In summary, the guiding catheter devices available suffer from various problems, such as lack of support, complexity, skill required to use, and difficulty of cannulation. Therefore, there exists the need for a device, system and method that allow the use of a guiding catheter that is easy to cannulate while also providing sufficient support.

SUMMARY OF THE INVENTION

A guiding catheter support device for stabilizing a guiding catheter while positioned in a body of a patient is disclosed. In one embodiment the support device comprises a stabilizing wire, the stabilizing wire comprising an elongate part and a first fortified end disposed on a first end of the elongate part; wherein the stabilizing wire increases the rigidity of at least a portion of the guiding catheter and is configured to be inserted into a guiding catheter while the guiding catheter is in a vessel of a patient. The stabilizing wire may also be configured to change the shape of at least a portion of the guiding catheter. The support device may further comprise a securing element for securing the position of the stabilizing wire inside the guiding catheter.

In another embodiment the stabilizing wire further comprises a second fortified end disposed on a second end of the elongate part. The first fortified end and the second fortified end may differ in thickness, length, rigidity, or strength. Either end may be used as the distal end to advance in the guiding catheter depending on the fortification that is needed.

In one embodiment any guiding catheter may be used. In this embodiment the stabilizing wire is inserted into the lumen beside the guidewire.

In another embodiment a specialized guiding catheter is used comprising a primary lumen and a stabilization lumen. In this embodiment the primary lumen is used for the guidewire and stent catheter and the stabilization lumen is used for the stabilizing wire. The stabilization lumen has a blind end at its distal end preventing the stabilizing wire from exiting out of the distal end of the catheter.

A method for stabilizing a guiding catheter is also disclosed, comprising positioning a guiding catheter in a vessel of a patient and then inserting a stabilizing wire into the guiding catheter; wherein the stabilizing wire increases the rigidity of at least a portion of the guiding catheter thereby stabilizing the catheter. The method may further comprise securing the position of the stabilizing wire inside the guiding catheter using a securing element. The method may include using a standard guiding catheter or using a specialized guiding catheter comprising a primary lumen and a stabilization lumen; wherein the stabilization lumen has a blind end at its distal end and the stabilizing wire is inserted into the stabilization lumen.

This, and further aspects of the present embodiments, are set forth herein.

BRIEF DESCRIPTION OF THE DRAWINGS

The invention has other advantages and features which will be more readily apparent from the following detailed description of the invention and the appended claims, when taken in conjunction with the accompany drawings, in which:

DETAILED DESCRIPTION OF THE PREFERRED EMBODIMENTS

Although the detailed description contains many specifics, these should not be construed as limiting the scope of the invention but merely as illustrating different examples and aspects of the invention. It should be appreciated that the scope of the invention includes other embodiments not discussed in detail herein. Various other modifications, changes and variations which will be apparent to those skilled in the art may be made in the arrangement, operation and details of the method and apparatus of the present invention disclosed herein without departing from the spirit and scope of the invention as described here.

Embodiments of the present invention relate to devices, systems, and methods for providing support for and stabilizing a guiding catheter while positioned in a vessel of a patient. The system comprises a guiding catheter and a stabilizing wire. The stabilizing wire comprises an elongate part and a fortified end disposed on a distal end of the elongate part, wherein the fortified end is more rigid than the elongate part. The stabilizing wire is configured to be inserted into the guiding catheter while the guiding catheter is in a vessel of a patient. The stabilizing wire increases the rigidity of at least a portion of the guiding catheter and curves at least a portion of the guiding catheter. This stabilizes the guiding catheter and prevents it from disengaging from the ostium of the target vessel.

Figures 1A, 1B:
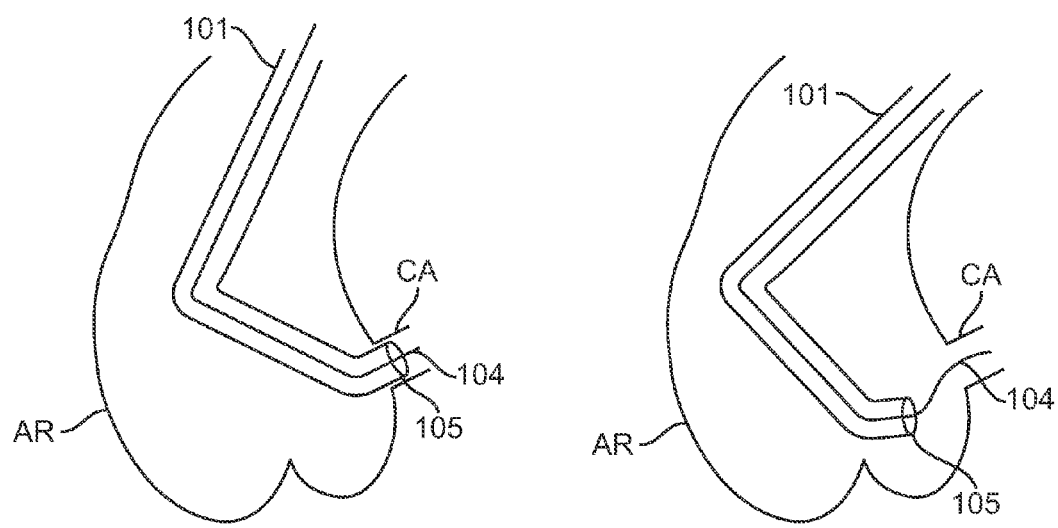
FIG. 1A shows a guiding catheter positioned at the ostium of a coronary artery without a stabilizing wire.
FIG. 1B shows a guiding catheter that has disengaged from the coronary artery.

A guiding catheter positioned at the ostium of a coronary artery without a stabilizing wire is shown in FIG. 1A. A guiding catheter 101 is advanced through the aorta AR to a coronary artery CA. The distal end 105 of the guiding catheter 101 is positioned at the ostium of the coronary artery CA. t a guidewire 104 is advanced through the guiding catheter 101 into the coronary artery CA.

FIG. 1B shows a guiding catheter 101 that has disengaged from the coronary artery CA. If force is applied to a guiding catheter 101, such as when a stent catheter is advanced through the guiding catheter 101, the distal end 105 often disengages from the ostium of the target vessel.

Figure 2:
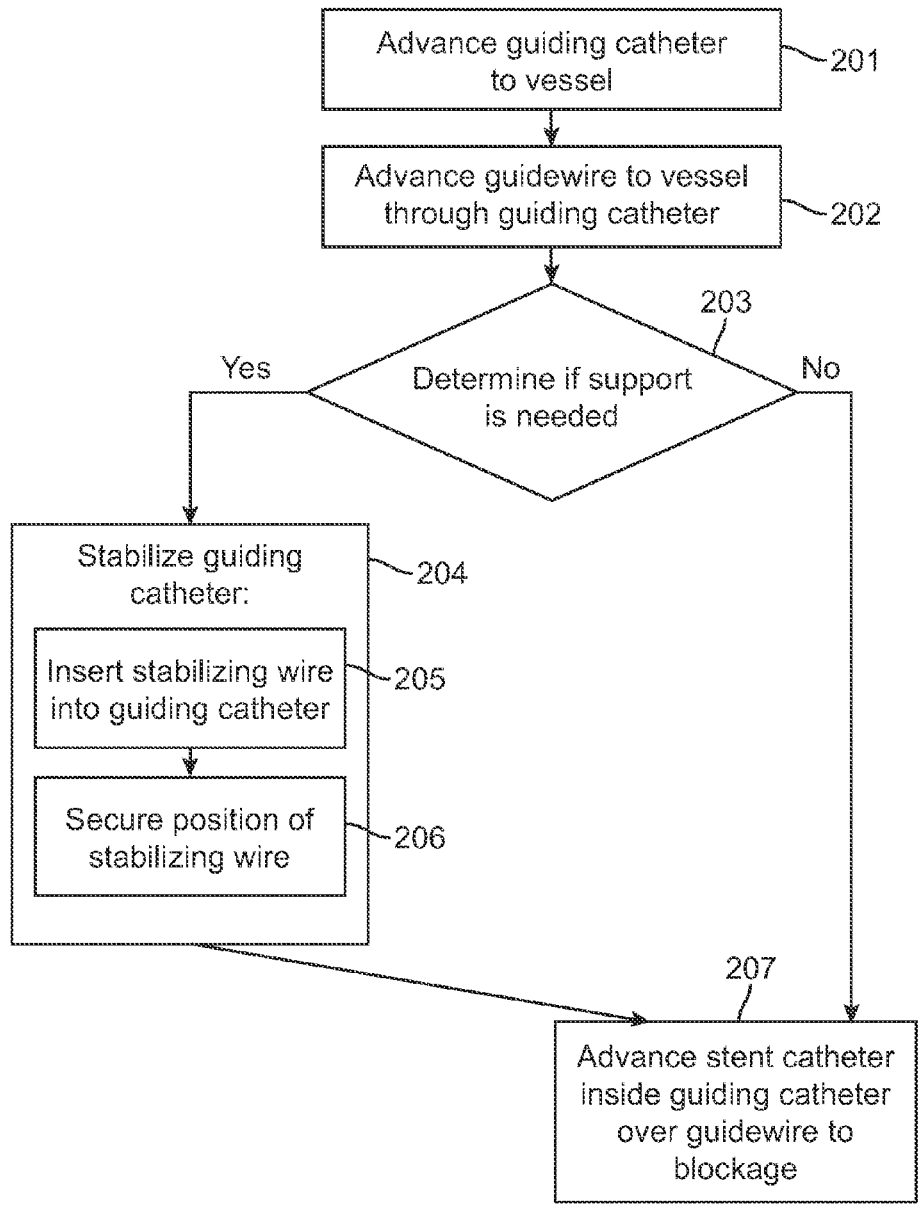
FIG. 2 is a flow diagram illustrating an exemplary method of securing a guiding catheter in a vessel of a patient with a stabilizing wire.
Figure 3:
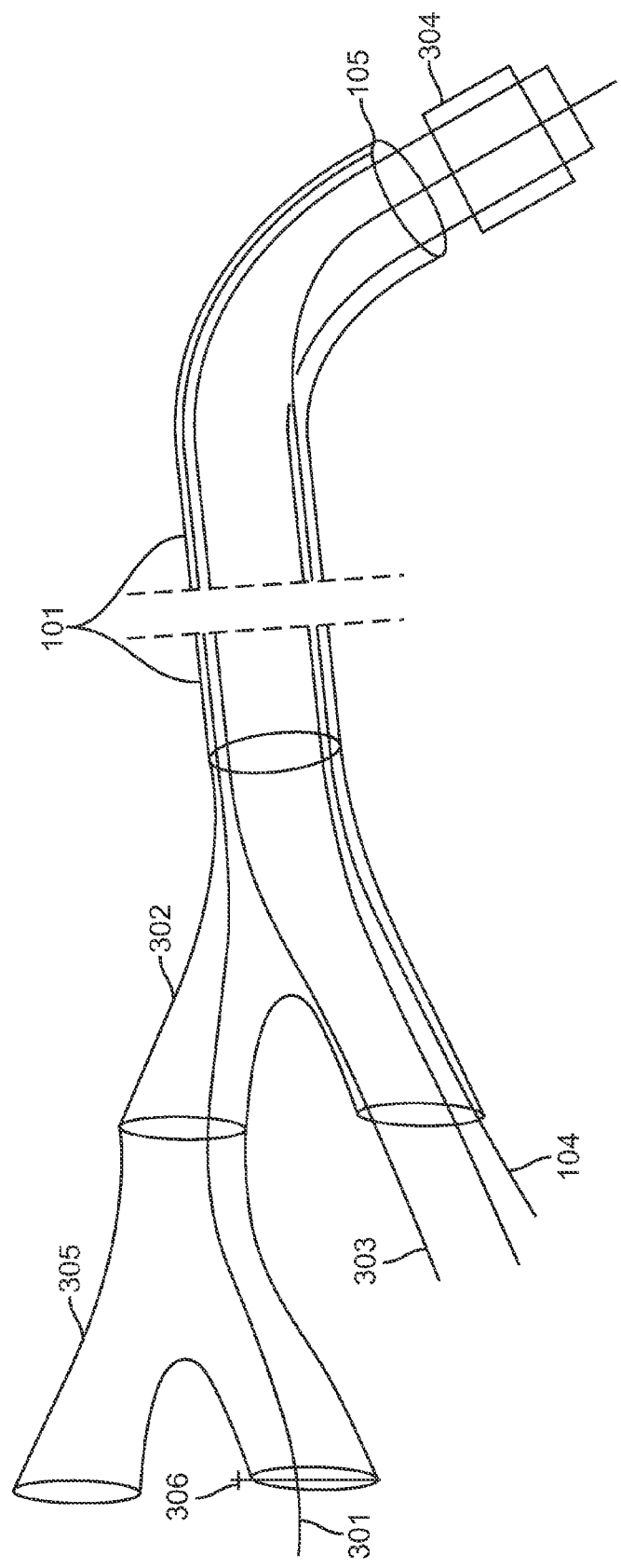
FIG. 3 shows an embodiment of a guiding catheter with a stabilizing wire and a stent catheter.

A flow diagram illustrating an exemplary method of securing a guiding catheter in a vessel of a patient using the present system and device is shown in FIG. 2 (structures shown in FIG. 3). At step 201, the guiding catheter 101 is advanced to the target vessel. The target vessel may be a coronary artery, a renal artery, a carotid artery, a limb vessel, or other blood vessel. Various types of guiding catheters 101 may be used such as Judkins catheters, Amplatz catheters, multipurpose guiding catheters, hockey stick catheters, Voda® catheters and Q-Curve® catheters manufactured by Boston Scientific Corporation located in Boston, Mass., or others known in the art. Optionally, as described below, a specialized guiding catheter may be used.

When the guiding catheter 101 is positioned at the ostium of the target vessel, the distal end of a Y connector 302 is connected to the proximal end of the guiding catheter 101. One of the proximal ends of the Y connector 302 is then connected to a manifold (not shown). At step 202, a guidewire 104 is advanced through the unconnected proximal end of the Y connector 302, into the guiding catheter 101, to the target vessel and past the blockage BL.

At step 203, the operator determines whether support is needed to keep the guiding catheter 101 in place. Alternatively this step may be performed before the guidewire 104 is advanced past the blockage BL. If it is determined that no support is needed, then at step 207, a stent catheter 303 is advanced through the Y connector 302 along the guidewire 104, inside the guiding catheter 101, into the target vessel, to the blockage BL. A balloon catheter without a stent 304 may alternatively be used. The stent catheter 303 or balloon catheter may be an over-the-wire type or a rapid exchange type.

Alternatively, if it is determined that support is needed, at step 204, the operator will stabilize the guiding catheter. Step 204 further comprises sub-steps 205 and 206. At sub step 205, the operator disconnects the proximal end of the Y connector 302 from the manifold (not shown). The distal end of a second Y connector 305 is then connected to the proximal end of the first Y connector 302 that was connected to the manifold. The manifold is then connected to one of the proximal ends of the second Y connector 305.

Thereafter, a stabilizing wire 301 is inserted through the unconnected proximal end of the second Y connector 305 through the first Y connector 302, into the guiding catheter 101 to the distal end 105 of the guiding catheter 101. In one embodiment, under fluoroscopy, the stabilizing wire 301 is advanced towards the distal end 105 of the guiding catheter 101. The advancement is stopped short of the distal end (about 1 cm short of the distal end 105) to ensure that the stabilizing wire 301 does not exit the guiding catheter and damage the vessel. In embodiments where a standard guiding catheter is used such as a Judkins catheter, Amplatz catheter, multipurpose guiding catheter, etc., the stabilizing wire 301 is advanced inside the lumen beside the traditional guidewire 104. In embodiments where a specialized guiding catheter 510 comprising a primary lumen 501 and a stabilization lumen 502 (shown in FIG. 5) is used, the stabilizing wire 301 is advanced inside the stabilization lumen 502.

At sub-step 206, the position of the stabilizing wire 301 inside the guiding catheter is then secured with a securing element 306. The securing element 306 may be part of the second Y connector 305 or it may be a separate device. In one embodiment, a valve disposed on the second Y connector 305 is closed to secure the position of the stabilizing wire 301. Optionally or additionally, a torque device may be used to secure the stabilizing wire 301. Once the stabilizing wire 301 is secured, the stabilizing wire 301 enables superior support of the guiding catheter 101 by increasing the rigidity of at least a portion of the guiding catheter 101. The additional rigidity prevents the guiding catheter 101 from prolapsing. In one embodiment, the stabilizing wire 301 increases the rigidity of the distal portion of the guiding catheter 101. By changing the rigidity of the guiding catheter 101, the stabilizing wire 301 may also reshape the distal portion of the guiding catheter such that in one embodiment, the guiding catheter 301 rests on the opposite wall of the aorta AR. The securing element 306 prevents the stabilizing wire 301 from exiting the guiding catheter 101 and damaging the vessel as well as ensuring that the support provided by the stabilizing wire 301 remains at an intended location.

After the guiding catheter 101 has been stabilized, in step 207, the stent catheter 303 is advanced through the first Y connector 302 along the guidewire 104, inside the guiding catheter 101, into the target vessel, to the blockage BL. A balloon catheter without a stent 304 may alternatively be used. The stent catheter 303 or balloon catheter may be an over-the-wire type or a rapid exchange type. The additional support provided by the stabilizing wire 301 stabilizes the guiding catheter 101 while the stent catheter 303 is advanced to the blockage BL.

The stabilizing wire 301 constructed according to the principles of the present invention comprises an elongate part and at least one fortified end disposed on an end of the elongate element. The thickness, length, rigidity, strength, or material of the fortified end may vary depending on the fortification that is needed. The elongate part and the fortified end may differ in thickness, length, rigidity, strength, or material. In one embodiment, the elongate part is less rigid than the fortified end. In another embodiment the fortified end has a length within a range of 2 to 10 cm long. The elongate part may be thinner than the fortified end, therefore providing more room in the guiding catheter for other equipment or fluid flow.

In one embodiment, the stabilizing wire 301 may comprise a first fortified end 307, an elongate middle part 309, and a second fortified end 308, wherein the first and the second fortified ends 307, 308 are disposed on the opposite ends of the elongate middle part 309. The thickness, length, rigidity, strength, or material of the two fortified ends 307, 308 may differ. The elongate middle part 309 may differ in thickness, length, rigidity, strength, or material from either fortified ends 307, 308. The operator may use either end 307, 308 as the distal end to advance in the guiding catheter 101 depending on the fortification that is needed. This allows the purchase of a single stabilization wire for use in situations with different fortification requirements. In one embodiment the first end 307 is 4 cm long, the middle part 309 is 120 cm long, and the second end 308 is 6 cm long. The shorter first end 307 may be stronger or more rigid than the longer second end 308.

The stabilizing wire 301 may be made of stainless steel, cobalt alloy, nickel-titanium, or any biocompatible material with suitable mechanical properties that are well known in the art for surgical applications. Depending on the type of guiding catheter 101 used, different amounts of fortification may be required. For example, guiding catheters that have more elaborate distal parts may require a longer fortified portion. Since they have longer, more complex distal forms the fortification is not required to be as rigid. This will allow for better maneuverability of the stabilizing wire. Other guiding catheters 101 may require shorter, stronger fortification. The stabilizing wire or the entire system may be heparin coated.

Figure 4:
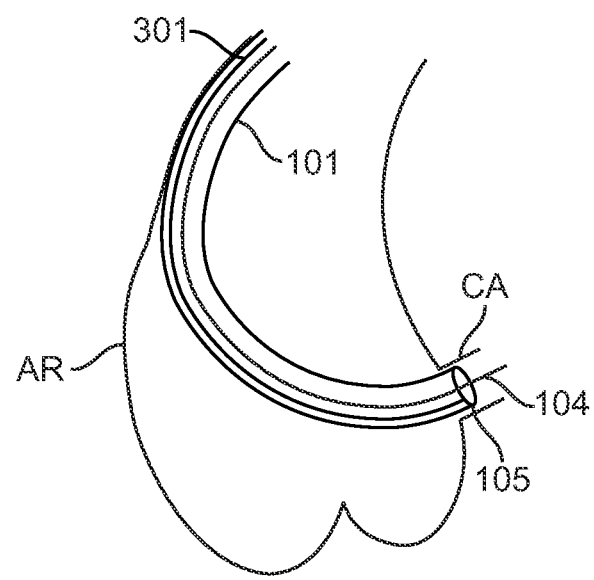
FIG. 4 shows an embodiment of a guiding catheter stabilized at the ostium of a coronary artery with a stabilizing wire.

An embodiment of a guiding catheter with a stabilizing wire is shown in FIG. 4. A stabilizing wire 301 is inserted in the guiding catheter 101 to the distal end 105. The stabilizing wire 104 curves the guiding catheter so that the guiding catheter rests along the opposite side of the aorta AR. The additional support provided by the stabilizing wire 301 holds the distal end 105 in place at the coronary artery CA and prevents prolapsing of the guiding catheter 101 into the left ventricle.

When the target vessel is a coronary artery CA or a renal artery the guiding catheter rests on the opposite wall of the aorta AR for support. In other target vessels such as carotids or limb vessels, however, there is no possibility of resting the guiding catheter 101 on the opposite wall of the aorta AR. In such situations the guiding catheter 101 is facing the obstructive vessel with the blockage BL and the operator frequently needs solid support.

Figure 5:
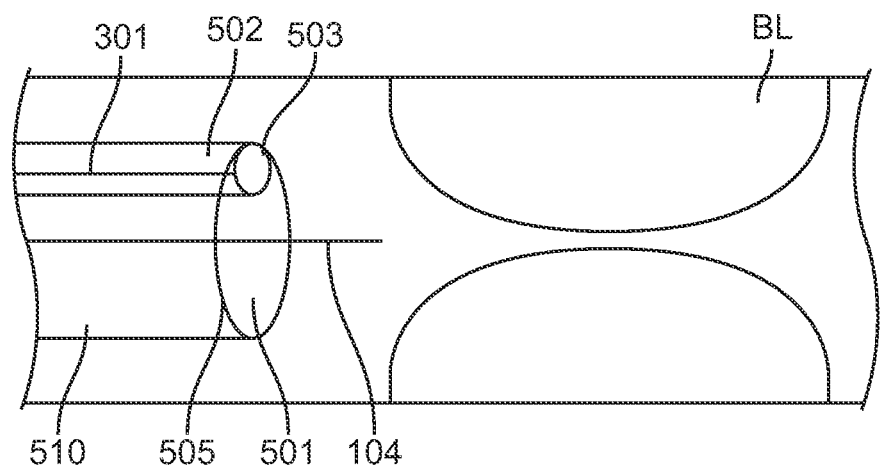
FIG. 5 shows an embodiment of a guiding catheter with a stabilization lumen.

In circumstances where it is impractical or impossible to rest or support the guiding catheter on a body vessel, a guiding catheter with a stabilization lumen as shown in FIG. 5 may be used. As seen in FIG. 5, a guiding catheter 510 is shown facing a blockage BL in a vessel. The guiding catheter 510 comprises two lumens, a primary lumen 501 and a stabilization lumen 502. The guidewire 104, and later the stent catheter 303 (shown in FIG. 3), are advanced through the primary lumen 501. The stabilization lumen 502 may be defined from the proximal end to the distal end 505 of the guiding catheter 510. The stabilizing wire 301 is advanced through the stabilization lumen 502 to the distal end 505 of the guiding catheter 510. In one embodiment, the guiding catheter 510 is advanced initially without the stabilizing wire 301. This allows the guiding catheter to have more flexibility so that it can more easily be navigated to the target location. After the guiding catheter 510 has reached the target location the stabilizing wire 301 may be inserted through the stabilization lumen 502 to provide additional support.

The stabilization lumen 502 may have a blind end 503 at the distal end 105 of the guiding catheter 510. The blind end 503 prevents the stabilizing wire 301 from exiting at the distal end 505 of the guiding catheter 510. Alternatively, the stabilization lumen 502 may terminate before the distal end 505 of the guiding catheter. The guiding catheter 510 may be made of a flexible polymer or other flexible biocompatible materials known in the art.

Figure 6:
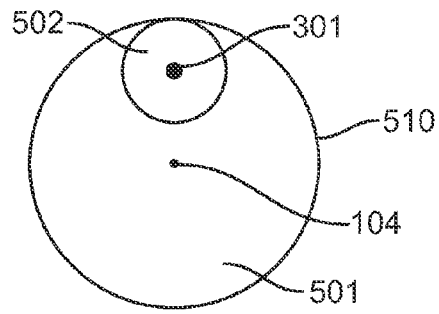
FIG. 6 shows cross sections of various embodiments of a guiding catheter with a stabilization lumen.
Figure 6:
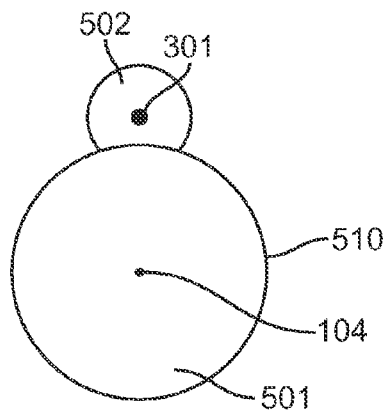
Figure 6:
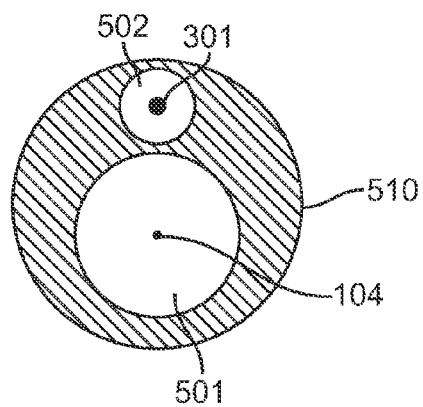
Figure 7:
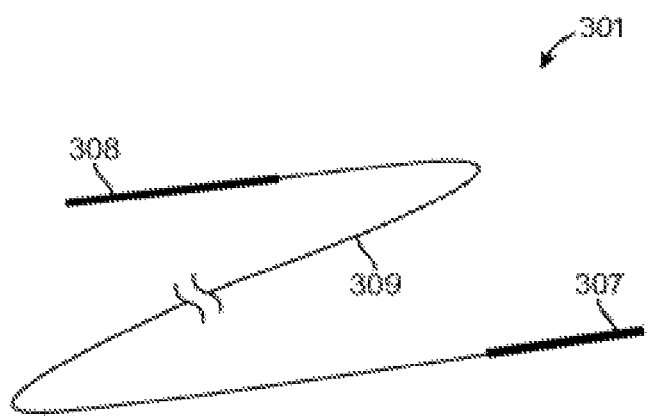
FIG. 7 shows an embodiment of a stabilizing wire.

Cross sections of various embodiments of a guiding catheter with a stabilization lumen are shown in FIG. 6. The guiding catheter 510 comprises a primary lumen 501 and a stabilization lumen 502. The primary lumen 501 is configured to receive the guidewire 104. The stabilization lumen 502 is configured to receive the stabilizing wire 301. In one embodiment the stabilization lumen 502 is disposed within the primary lumen 501. In other embodiments the stabilization lumen 502 is outside the primary lumen 501. Additionally and optionally, the stabilization lumen 502 comprises a distal blind end such that the stabilizing wire is prevented from exiting the stabilization lumen and damaging the vessel. The lumens may be circular, semicircular, oval, elliptical, oblong, triangular, rectangular or any arbitrary shapes or configurations. It is further contemplated that the catheter may comprise additional lumens to receive additional stabilizing wires.

The guiding catheter support devices, systems, and methods as described herein allow the use of a guiding catheter that is easy to engage while also providing support and preventing the guiding catheter from disengaging from the target vessel. The devices, systems, and methods allow the operator to avoid removal of the equipment or abandoning the case when it is determined that more support is needed. The duration of the procedure and radiation exposure may also be reduced.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A guiding catheter system, comprising:
   a guiding catheter comprising a proximal end, a distal end, a primary lumen and a secondary lumen; and
   a stabilizing wire comprising an elongate part and a first fortified end disposed on a first end of the elongate part, wherein the first fortified end forms a first end of the stabilizing wire and is more rigid than the elongate part;
   wherein the secondary lumen extends the entire length of the guiding catheter and has a distal blind end at a distal edge of the distal end of the guiding catheter; and
   wherein the stabilizing wire is configured to be inserted into the secondary lumen to the blind end while the guiding catheter is at an ostium of a vessel of a patient such that the first fortified end of the stabilizing wire increases the rigidity of at least a portion of the guiding catheter thereby preventing the guiding catheter from disengaging from the ostium of the vessel; and
   wherein the first fortified end of the stabilizing wire is configured to change the shape of at least a portion of the guiding catheter when the first fortified end of the stabilizing wire is inserted such that the guiding catheter rests on a wall of the aorta opposite an ostium of a coronary artery.

2. The system of claim 1, further comprising a securing element at the proximal end of the guiding catheter; wherein the securing element secures the stabilizing wire at a position inside the guiding catheter.

3. The system of claim 1, wherein a distal portion of the guiding catheter is configured to comprise two bends before the stabilizing wire is inserted and wherein the stabilizing wire is configured to change the shape of the distal portion such that the distal portion forms a single curve.

4. A guiding catheter system, comprising:
   a guiding catheter comprising a proximal end, a distal end, a primary lumen and a secondary lumen; and
   a stabilizing wire comprising an elongate part, a first fortified end disposed on a first end of the elongate part, and a second fortified end disposed on a second end of the elongate part, wherein the first fortified end forms a first end of the stabilizing wire and is more rigid than the elongate part, wherein the second fortified end forms a second end of the stabilizing wire and is more rigid than the elongate part, and wherein the first fortified end is shorter and more rigid than the second fortified end;
   wherein the secondary lumen extends the entire length of the guiding catheter and has a distal blind end at a distal edge of the distal end of the guiding catheter; and
   wherein the stabilizing wire is configured to be inserted into the secondary lumen to the blind end while the guiding catheter is at an ostium of a vessel of a patient such that the first fortified end of the stabilizing wire increases the rigidity of at least a portion of the guiding catheter thereby preventing the guiding catheter from disengaging from the ostium of the vessel.

5. A method for stabilizing a guiding catheter, comprising:

positioning a guiding catheter comprising a primary lumen and a stabilization lumen at an ostium of a vessel of a patient;

inserting a stabilizing wire comprising an elongate part and a first fortified end disposed on a first end of the elongate part into the stabilization lumen after the guiding catheter has been positioned at the ostium of the vessel;

advancing the stabilization wire to a distal blind end of the stabilization lumen at a distal edge of the guiding catheter thereby stabilizing the positioned guiding catheter and preventing the guiding catheter from disengaging from the ostium of the vessel; and advancing a stent catheter through the primary lumen into the vessel;

wherein the first fortified end forms a first end of the stabilizing wire and is more rigid than the elongate part; and wherein the first fortified end of the stabilizing wire increases the rigidity of at least a portion of the guiding catheter thereby stabilizing the catheter; and wherein the vessel is a coronary artery and wherein the first fortified end of the stabilizing wire changes the shape of at least a portion of the guiding catheter when the stabilizing wire is inserted such that the guiding catheter rests on a wall of the aorta opposite the ostium of the coronary artery.

6. The method of claim 5, further comprising securing a position of the stabilizing wire inside the guiding catheter with a securing element at the proximal end of the guiding catheter.

7. The method of claim 6, wherein the stabilizing wire further comprises a second fortified end disposed on a second end of the elongate part, wherein the second fortified end forms a second end of the stabilizing wire and is more rigid than the elongate part.

8. The method of claim 6, wherein the guiding catheter is a Judkins catheter or an Amplatz catheter.

9. The method of claim 5, wherein the stabilizing wire further comprises a second fortified end disposed on a second end of the elongate part, wherein the second fortified end forms a second end of the stabilizing wire and is more rigid than the elongate part.

10. The method of claim 5, wherein a distal portion of the guiding catheter comprises two bends before the stabilizing wire is inserted and wherein the stabilizing wire changes the shape of the distal portion such that the distal portion forms a single curve.

* * * * *